United States Patent [19]

Spanswick et al.

[11] Patent Number: 4,709,080

[45] Date of Patent: Nov. 24, 1987

[54] POLYACYL ARYL ARYLATES

[75] Inventors: James Spanswick, Wheaton; George E. Kuhlmann, Lisle, both of Ill.

[73] Assignee: Standard Oil Company, Chicago, Ill.

[21] Appl. No.: 918,834

[22] Filed: Oct. 14, 1986

Related U.S. Application Data

[63] Continuation of Ser. No. 520,637, Aug. 8, 1983, abandoned, which is a continuation of Ser. No. 345,661, Feb. 4, 1982, abandoned, which is a continuation of Ser. No. 812,816, Jul. 5, 1977, abandoned.

[51] Int. Cl.$^4$ .............................................. C07C 69/80
[52] U.S. Cl. ........................................ 560/86; 560/77
[58] Field of Search ..................................... 560/77, 86

[56] References Cited

U.S. PATENT DOCUMENTS

| | | | |
|---|---|---|---|
| 1,979,559 | 11/1934 | Kyrides | 560/86 |
| 2,653,165 | 9/1953 | Levine | 560/77 |
| 2,833,816 | 5/1958 | Saffer et al. | 560/77 |

*Primary Examiner*—Werren B. Lone
*Assistant Examiner*—Vera C. Clarke
*Attorney, Agent, or Firm*—William H. Magidson; Ralph C. Medhurst

[57] ABSTRACT

Aryl arylate esters substituted with an acyl moiety on both the aryl and arylate groups of said esters which can be produced by the oxidation of alkyl substituted aryl arylate esters using a heavy metal/bromine catalyst.

2 Claims, No Drawings

POLYACYL ARYL ARYLATES

This is a continuation of application Ser. No. 520,637, filed Aug. 8, 1983, which in turn is a continuation of Ser. No. 345,661 filed Feb. 4, 1982, which in turn is a continuation of Ser. No. 812,816 filed July 5, 1977, now all abandoned.

This invention relates to aryl arylate esters substituted with an acyl moiety on both the aryl and arylate groups of said ester and methods of producing said esters. More particularly, this invention relates to 4,4'-diacylphenyl benzoates and methods of producing these compounds.

U.S. Pat. Nos. 3,804,805 and 3,778,410 of Kuhfuss et al. describe a process of producing self-reinforcing copolyesters by reacting polyesters, preferably polyethyleneterephthalate, with an acyloxy substituted aromatic acid, such as p-acetoxybenzoic acid. The patentees indicate (column 2, lines 1 to 11 of the U.S. Pat. No. 3,804,805 that, unlike other polyesters, these copolyesters are suitable for the production of molded objects capable of high strength service without the presence of a reinforcing agent such as glass fibers. While these polyesters have many advantageous properties, they are expensive due to the high cost of the acyloxybenzoic acid. The patentees indicate that the copolyester must be prepared from the acyloxybenzoic acid and cannot be produced from the corresponding hydroxybenzoic acid, since, if the prior art process of reacting hydroxybenzoic acid, terephthalic acid and ethylene glycol is employed, there is a substantial number of ether linkages formed between the ethylene glycol moiety and the hydroxy moiety of the hydroxybenzoic acid. Apparently the aliphatic to aromatic ether groups have a deleterious effect on the polymer properties and the self-reinforcing properties are not attained. Accordingly, there is a need for a method of producing copolyesters of this type from monomers other than acyloxybenzoic acids.

The general object of this invention is to provide relatively inexpensive copolymerizable monomers containing hydroxyarylenecarboxylic acid moieties. A more specific object of this invention is to provide relatively inexpensive copolymerizable monomers containing hydroxyarylenecarboxylic acid moieties capable of polyesterification with aliphatic glycols without the formation of undesirable aliphatic to aromatic ether linkages.

For the purpose of this invention, the term "arylate" is used in a manner common in the polyester field to describe an aromatic carboxylic acid ester of an aromatic hydroxy compound.

We have now found that aryl arylates containing an acyl group on both the aryl and arylate moieties are relatively inexpensive precursors for the production of the polyesters of the type described by Kuhfuss et al. These aryl arylate esters can be produced inexpensively by oxidizing the alkyl groups on esters formed from alkyl substituted aromatic hydroxy compounds and alkyl substituted aromatic acids. For example, an extremely inexpensive precursor containing only terephthalic acid moieties and parahydroxy benzoic acid moieties can be produced by oxidizing the esterification product of paratoluic acid and paracresol. The oxidation product is 4,4'-dicarboxyphenyl benzoate. Since both paratoluic acid and paracresol are readily available inexpensive raw materials, it is clear that the resultant 4,4'-dicarboxyphenyl benzoate can be produced inexpensively in contrast to the paraacyloxybenzoic acid employed in the process of Kuhfuss et al.

While Takata et al. [Kokkaido Daigaku Kogakubu Kenkyu Holoku 54 (1969) 325] theorize that 4,4'-dicarboxyphenyl benzoate is formed as an intermediate in the Baeyer-Villiger oxidation of benzophenone carboxylic acids, Takata et al. do not disclose isolation of 4,4'-dicarboxyphenyl benzoate but only obtain a mixture of terephthalic acid and para-hydroxybenzoic acid. Attempts by us to repeat the work reported in Takata's paper and analysis of the oxidation products prior to hydrolysis failed to indicate the production of any 4,4'-dicarboxyphenyl benzoic acid or its diethyl ester. Accordingly, it is highly improbable that this acid or its esters are produced.

The aryl arylates of this invention can be represented by the structure:

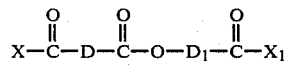

wherein D and $D_1$ are independently divalent arylene groups, such as phenylene, naphthalene, dibromophenylene, dimethoxyphenylene, nitrophenylene, sulfophenylene, carboxyphenylene, etc.; X and $X_1$ are independently halogen or $-OR$ and $-OR_1$ wherein R and $R_1$ are independently hydrogen, alkyl of from 1 to 24 carbon atoms, such as methyl and tetracosyl alkenyl of from 2 to 24 carbon atoms, such as vinyl, allyl, oleyl, etc.; aryl of from 6 to 24 carbon atoms, such as phenyl, p-octadecylphenyl, etc.; aralkyl of from 7 to 24 carbon atoms such as benzyl; hydroxyalkyl such as hydroxyethyl, 2-hydroxypropyl, etc.; polyoxyethylene glycol moieties, polyoxypropylene glycol moieties, etc.

The aryl arylates of this invention having at least one acyl moiety on both the aryl and arylate rings can be produced by the oxidation of polyalkyl substituted aryl arylates having alkyl groups on both the aryl and arylate rings using a bromide/heavy metal catalyst system of the type described in U.S. Pat. No. 2,833,816, which is incorporated by reference. Surprisingly we have found that it is possible to oxidize the alkyl groups on aromatic rings to free carboxylic acid groups without destruction of the ester groups of the aryl arylate esters. We have found that other oxidation systems employing acids and bases are generally unsuitable for the oxidation of the polyalkyl aryl arylates since under the acidic or alkaline conditions normally employed for most oxidations, there is saponification of the internal ester linkage and the desired compounds of this invention are not obtained.

The polyalkyl substituted aryl arylates useful for producing the compounds of this invention can have the structure:

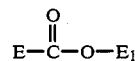

wherein E and $E_1$ are independently aryl groups containing from 1 to 5 substituents selected from the group consisting of alkyl groups of from 1 to 4 carbon atoms (methyl, ethyl, propyl, isopropyl, butyl), halo groups (chloro, bromo, iodo, fluoro), nitro groups, amine groups, sulfonic acid groups, alkoxy groups containing from 1 to 4 carbon atoms such as methoxy, ethoxy, propoxy, butoxy, etc. Generally, these groups are meta or para to the ester group joining the aromatic rings. During the oxidation, the alkyl substituents are converted to carboxylic acid groups, amino ($NH_2$) groups are converted to nitro groups, while halogen groups, alkoxy groups, nitro groups and sulfonic acid groups are unaffected by the oxidation. In general, it is preferred that E and $E_1$ are each substituted with a single methyl group in order to provide an aromatic compound containing two free carboxylic acid groups. In those cases where trifunctional or tetrafunctional acids are desired, E and $E_1$ can be substituted with a total of 3 or 4 alkyl groups, preferably methyl groups.

Suitable polyalkyl substituted aryl arylates useful for producing the compounds of this invention include 4,4'-dimethyl-phenylbenzoate, 3,4,4'-trimethyl-phenylbenzoate, 3,4,3',4'-tetramethyl-phenylbenzoate, 4,4'-diethyl-phenylbenzoate, 3,2'-dichloro-4,4'-dimethyl-phenylbenzoate, 2,1'-dibromo-4,4'-dimethyl-phenylbenzoate, 3,2'-dinitro-4,4'-dimethylphenylbenzoate, 3-amino-4,4'-dimethyl-phenylbenzoate, 2-sulfo-4,4'-dimethyl-phenylbenzoate, 3,2'-dimethoxy-4,4'-dimethyl-phenylbenzoate, 6,4'-dimethyl-naphthyl benzoate, 6,6'-dimethyl-naphthyl beta-naphthoate, etc.

The polyalkyl substituted aryl arylates can be produced by esterification of an alkyl substituted aromatic monocarboxylic acid and an alkyl substituted aromatic monohydroxy compound, such as the technique described by Lowrance in U.S. Pat. No. 3,772,389, which is incorporated by reference. In this process, the alkyl substituted aromatic monohydroxy compound is esterified with an alkyl substituted aromatic monocarboxylic acid compound in the presence of a catalytic amount of borate-sulfuric acid catalyst complex at a temperature of from about 75° C. to 285° C. If desired, various other techniques for producing the polyalkyl substituted aryl arylates can be employed such as the techniques described in D. Hausigh Liebigs Ann. 726 216 (1969), J. F. Kirsh et al. J. Org. Chem. 33 127 (1968), and W. Autenrieth & G. Thomae Ber. 57B 423 (1924) which are all incorporated by reference.

Suitable alkyl substituted aromatic monohydroxy compounds useful for preparing the polyalkyl substituted aryl arylates include para-cresol, meta-cresol, ortho-cresol, 3,4-dimethylphenol, para-ethylphenol, metachloro-para-cresol, ortho-bromo-para-methylphenol, meta-nitro-para-methylphenol, meta-amino-para-methylphenol, ortho-sulfo-para-methylphenol, meta-methoxy-para-methylphenol, 6-methyl-alphanaphthol, 3,4,5-trimethylphenol, etc.

Suitable alkyl substituted aromatic monocarboxylic acids useful for preparing the polyalkyl aromatic arylates include ortho-toluic acid, meta-toluic acid, para-toluic acid, 3,4-dimethylbenzoic acid, 4-ethylbenzoic acid, metachloro-paramethylbenzoic acid, orthobromo-paramethyl-benzoic acid, metanitro-paramethylbenzoic acid, metaamino-parabenzoic acid, metasulfo-paramethylbenzoic acid, meta-methoxy-para-methylbenzoic acid, 6-methyl-betanaphthoic acid.

In somewhat greater detail, the aryl arylate esters having acyl moieties on each aromatic ring can be produced by reacting a polyalkyl substituted aryl arylate having alkyl groups on both the aryl and arylate rings in a liquid phase with molecular oxygen in the presence of a catalyst comprising a bromine containing compound and a heavy metal oxidation catalyst. The reaction is preferably carried out in a saturated aliphatic monocarboxylic acid medium which is relatively stable during the oxidation reaction, provided by an acid containing from 1 to 8 carbon atoms, such as formic acid, acetic acid, propionic acid, butyric acid, octanoic acid, etc.

Suitable heavy metal compounds of the catalyst include manganese, cobalt, nickel, chromium, vanadium, molybdenum, tungsten, tin, cerium, etc., which may be employed in the elemental, combined or ionic form. Various combinations of these heavy metals can be employed such as mixtures of manganese and cobalt. The bromine component of the catalyst can be added in elemental, combined or ionic form. Suitable sources of bromine include ammonium bromide, salts of bromine with a heavy metal (manganese bromide, nickel bromide, etc.), bromine, hydrogen bromide, potassium bromate, organic bromine containing compounds such as tetrabromoethane, benzylbromide, etc. These catalyst components can be used in a concentration of about 0.0001 to 0.2 moles of heavy metal and bromine per mole of the polyalkyl substituted aryl arylate ester.

The reaction temperature should be sufficiently high so that the desired oxidation reaction occurs and not so high as to cause undesirable side reactions or charring of the reactants. For example, while the oxidation can be carried out at a temperature of 120° to 275° C., it is generally preferable to carry out the oxidation at a temperature of about 130° to 180° C. for maximum yields. Above about 180° C. there is a tendency for hydrolysis of the ester linkage of the aryl arylate ester and a correspondent reduction in yields of the desired compounds.

Oxygen can be used in the form of substantially 100% oxygen gas or in a form of gaseous mixtures containing lower concentrations of oxygen such as, for example, air.

The oxidation process is generally carried out under essentially liquid phase conditions and accordingly the temperature and pressure should be regulated to provide a liquid phase in the reaction zone. Generally the pressure may be in the range of atmospheric up to 1500 psig.

The aryl arylates having at least two free carboxylic acid groups can be derivatized by conventional means, such as to the polyacyl halides by reaction with thionyl chloride, sulfuryl chloride, phosphorus pentachloride, etc.; esterified by reaction of the free acid or polyacyl halides with a suitable monohydroxy compound at a temperature of 0° to 40° C.; transesterified by reacting the free acids with trialkyl orthoformates (trimethyl orthoformate or triethyl orthoformate) at a temperature of 200° to 220° C.; or the polymethyl ester produced first by one of the aforesaid reactions or by conversion with diazomethane and the appropriate monomeric polyester produced by transesterification with a suitable monohydroxy compound.

Suitable monohydroxy compounds useful for forming monomeric esters described above include alcohols containing from 1 to 24 carbon atoms such as methyl alcohol, ethyl alcohol, isopropyl alcohol, propyl alcohol, allyl alcohol, methallyl alcohol, n-butyl alcohol, n-hexyl alcohol, n-octyl alcohol, 2-ethylhexyl alcohol, decyl alcohol, tridecyl alcohol, stearyl alcohol, oleyl alcohol, tetracosyl alcohol; aromatic hydroxy compounds containing from 6 to 24 carbon atoms such as phenol, cresol, para-stearylphenol, naphthol, etc., benzyl alcohol, etc.

These esters can be produced under conventional reaction conditions by reacting from about 1 to 10 mols of monohydroxy compound per acyl equivalent of said polyacyl substituted aryl arylate ester to form a solution of the desired polyester in monohydroxy compound. If desired esterification catalysts or transesterification catalysts can be used, such as sulfuric acid, phosphoric acid, paratoluene sulfonic acid, benzene sulfonic acid, stannous octoate, boron trifluoride etherate, tetraalkyl titanates and zirconates of U.S. Pat. No. 3,056,818, etc.

The polymethyl and polyethyl esters can be conveniently prepared by refluxing the polyacyl substituted aryl arylate esters in a stoichiometric excess of trialkyl(-methyl or ethyl)orthoformate.

The polyhydroxyalkyl esters can be prepared by ester interchange of the polymethyl esters with ethylene glycol and propylene glycol to produce for example hydroxyethyl and 2-hydroxypropyl esters of the polyacyl substituted aryl arylates. If desired transesterification catalysts such as calcium acetate, magnesium acetate, antimony acetate, etc. can be used. Alternatively, the hydroxyalkyl esters can be produced by reacting the polyacid with ethylene oxide or propylene oxide in which case there will be a mixture of polyoxyethylene or polyoxypropylene glycol esters as well as the hydroxyethyl and hydroxypropyl esters.

The monomeric polyesters of this invention can be used as plasticizers of resinous polymers of vinyl chloride, such as homopolymeric polyvinyl chloride, the conventional 95-5 vinyl chloride-vinyl acetate copolymers, etc. The lower alkyl esters, the phenyl esters and the hydroxyalkyl esters can be used to produce high molecular weight polyesters, suitable for molding. The acyl halides can be used in interfacial polymerization with diamines, such as hexamethylene diamine and p-phenylene diamine to produce crystalline polycarbonamides.

The following examples are merely illustrative.

EXAMPLE I

Five-hundred grams acetic acid, 10 grams distilled water, 5.0 grams cobaltic acetate, 0.5 grams manganese acetate, 0.5 grams of 48% aqueous HBr and 150 grams 4,4'-dimethylphenylbenzoate were placed in a 2-liter titanium reactor equipped with a knock back reflux condenser, stirrer and air inlet line. The reactor was heated to 343° F. at 400 psig for 23 minutes with air being bubbled into the reactor at 0.8 cubic feet per minute. Steam was provided to cool the condenser at 25 psig (267° F.). The oxygen consumption was 115 mole percent of theory (complete conversion to diacid) and 0.5 moles of $CO_2$ was produced during oxidation. The reaction product was cooled and consisted of a slurry of a white precipitate having a reddish color apparently due to the cobalt component of the catalyst. The white precipitate was filtered, washed twice with 200 ml portions of acetic acid followed by 500 ml water and air dried to yield 172 grams of an off-white solid having a molecular weight by carboxylic determination of 287. The compound, which melted at 360° C., was 4,4'-dicarboxyphenylbenzoate which had a molecular weight of 287 by COOH determination (theoretical molecular weight of 286).

The 4,4'-dimethylphenylbenzoate used in this example was prepared by adding 108 grams para-cresol, 136 grams para-toluic acid, 2000 ml xylene, 2 ml 100% sulfuric acid and 2.4 grams boric acid to a 5000 ml liter equipped with mechanical stirrer and a Dean-Stark distillation receiver. The reactants were refluxed for ten hours during which time 17.5 ml water was collected in the Dean-Stark distilling receiver. A slight precipitate was filtered off and the filtrate was washed with 500 ml of 5% aqueous sodium carbonate, dried over sodium sulfate and concentrated by heating on an electric heating mantle. The oil-like concentrate was recrystallized from ethanol yielding 187 grams (82% theoretical) of 4,4'dimethylphenylbenzoate having a melting point of 92°–96° F. (literature melting point 92° C.).

EXAMPLE II

The process described in Example I was repeated using 500 grams acetic acid, 10 grams distilled water, 1.1 grams cobalt acetate, 0.54 grams manganese acetate, 1.0 grams of 48% aqueous HBr and 100 grams 4,4'-dimethylphenylbenzoate. The oxidation was carried out at 400° F. and 400 psig for 17 minutes yielding 578 grams of a beige precipitate and was isolated in the same manner as the product in Example 1. The oxygen consumption was 120 mole percent of theoretical and 0.5 moles $CO_2$ were produced. The initial molecular weight of the reaction product was 334 indicating substantial oxidation and hydrolysis of the desired 4,4'-dimethylphenylbenzoate to a mixture of dicarboxyphenylbenzoate, hydroxymethylbenzoic acid and terephthalic acid (oxidation of hydroxymethylbenzoic acid) due to the higher reaction temperature. The reaction product was then recrystallized from dimethylsulfoxide yielding two fractions, the less soluble mono carboxylic acid having a molecular weight of 357 and the more soluble diacid having a molecular weight of 294. The subsequent recrystallization of the more soluble material from propionic acid followed by recrystallization from N-methylpyrrolidone yielded the desired 4,4'-dicarboxyphenylbenzoate having a molecular weight of 282, 64.7% carbon and 3.62% hydrogen (theoretical 62.94% carbon and 3.49% hydrogen).

EXAMPLE III

This example illustrates the series of oxidation experiments on 4,4'-dimethylphenylbenzoate. The process described in Example I was repeated using the concentration of reactants set forth below in Table I. The results are also set forth below in Table I.

TABLE I

| | | | | | |
|---|---|---|---|---|---|
| 4,4'-Dimethyl-phenylbenzoate | 150 g | 150 g | 250 g | 200 g | 159 g |
| Cobalt acetate | 5 g | 5.0 g | 8.3 g | 6.7 g | 5.0 g |
| Manganous acetate | 0.5 g | 0.5 g | 0.8 g | 0.67 g | 0.5 |
| Distilled water | 10 g | 10 g | 10 g | 10 g | 10 g |
| 48% HBr | 0.5 g | 0.5 g | 0.8 g | 0.67 g | 0.5 |
| Acetic acid | 500 g | 500 g | 500 g | 500 g | 500 g |
| Pressure | 400 psi | 400 psig | 400 psi | 400 psi | 400 psi |
| Temperature °F. | 343° | 343° | 342° | 343° | 343° |
| Reactor effluent | 677 g | 665 g | 748 g | 718 g | 674 g |
| Run time | 22 min | 22 min | 29 min | 27 min | 24 min |
| $O_2$ uptake | 108 mole % | 103% | 95% | — | 106% |
| Yield diacid | 163 g | 164 g | 259 g | 224 g | 174 g |
| % yield | 85.7% | 86.5% | 81.8% | 88.3% | 87.8% |
| N.W. by —COOH analysis | 276.5 | 283 | 280 | 276.6 | 278 |
| Appearance | White | Off White (Pink) | Off White (Yellow) | Off White (Yellow) | White |

A composite of the above runs had a molecular weight by carboxyl analysis of 285 (theoretical 286).

Accordingly, the above runs illustrate that 4,4'-dimethylphenylbenzoate can be converted reproducibly to 4,4'-dicarboxyphenylbenzoate.

EXAMPLE IV

This example illustrates the production of the diacyl chloride of 4,4'-dicarboxyphenylbenzoate. One hundred grams 4,4'-dicarboxyphenylbenzoate, 500 grams thionyl chloride and 10 grams pyridine were refluxed together in a 2-liter flask, fitted with a stirrer and condenser, until a clear solution was obtained, 3 to 4 hours. The excess thionyl chloride was removed from the flask by distillation under vacuum and the pale yellow solid residue, recrystallized from benzene. The off-white platelets of the diacid chloride were filtered off and washed with heptane prior to drying in a vacuum oven. Yield 93 grams. M.P. 138°–142° C.

EXAMPLE V

This example illustrates the esterification of 4,4'-dicarboxyphenylbenzoate. Four grams 4,4'-dicarboxyphenylbenzoate were slurried with a 5% solution of dry hydrogen chloride in methanol, and stirred at 20° C. for 24 hours. The insoluble material was filtered off and the filtrate evaporated to dryness to yield an off-white solid. M.P. 150° C. to 200° C. Recrystallization from ethanol gave a white solid. M.P. 160°–170° C.

EXAMPLE VI

This example illustrates the esterification of 4,4'-dicarboxyphenylbenzoate using trimethylorthoformate. 4,4'-dicarboxyphenylbenzoate (5.72 grams) and trimethylorthoformate (5.1 grams) were mixed together in a 50 ml flask, fitted with a reflux condenser and stirrer, and heated to 210° C. in an oil bath. After six hours a further 5.1 grams of trimethylorthoformate was added and heating continued for eight hours. The reaction was cooled and the residue ground up and extracted with boiling toluene. The toluene soluble fraction was recrystallized from toluene to yield 1.75 grams of dimethyl ester of 4,4'-dicarboxyphenylbenzoate m.p. 171° to 172° C.

EXAMPLE VII

This example illustrates the production of a diphenyl ester of 4,4'-dicarboxyphenylbenzoate. A solution of 5.64 grams phenol and 4.8 grams pyridine in 100 ml xylene was azeotroped to dryness and cooled to 22° C. 9.69 grams of the diacid chloride of 4,4'-dicarboxyphenylbenzoate was added to the reaction which was stirred at 20° C. overnight. The diphenyl ester of 4,4'-dicarboxyphenylbenzoate white precipitate was filtered off and dried, m.p. 208°–212° C.

EXAMPLE VIII

This example illustrates the production of 4,4'-bis(2-hydroxyethyl)carboxyphenylbenzoate. 4,4'-dicarboxyphenylbenzoate, 28.6 grams; ethylene oxide, 9.7 grams; and triethylamine, 2 grams, were refluxed together in dimethylacetamide, 250 ml, for 3 hours. The solution was poured onto 750 ml of hot water and the precipitate filtered off, washed with acetone, then recrystallized from ethanol to give white solid 4,4'-bis(2-hydroxyethyl)carboxyphenylbenzoate, m.p. 85°–93° C.

EXAMPLE IX

This example illustrates the production of 4,4'-bis(2-hydroxyethyl)carboxyphenylbenzoate by the reaction of the dimethyl ester of 4,4'-dicarboxyphenylbenzoate with ethylene glycol. A mixture of the dimethylester of 4,4'-dicarboxyphenylbenzoate (160 grams) and ethylene glycol (47.4 grams) with calcium acetate, 0.15 grams and manganese acetate 0.15 grams was heated to 200° C. in a three-necked flask fitted with a stirrer and a vigruex column. Methanol was distilled out of the reaction over a five hour period as temperature was increased from 200° C. to 250° C. The total distillate was 23 grams. The melt was poured onto a metal tray and allowed to cool. The solid was extracted with ethanol, 2.5 liters, the residue was unreacted dimethyl ester. The filtrate on cooling yielded a white solid, m.p. 85°–95° C. It will be noted that the 4,4'-bis(2-hydroxyethyl)carboxyphenylbenzoate produced in Examples VIII and IX both have essentially the same melting point.

EXAMPLE X

This example illustrates the production of 4,4'-bis(2-hydroxyethyl)carboxyphenylbenzoate by the acyl halide route. Nineteen grams of the diacid chloride of 4,4'-dicarboxyphenylbenzoate was added to a solution of ethylene glycol 8.8 grams, and triethylamine 6.0 grams, in dimethylacetamide 100 ml. The resulting solution was stirred at 22° C. for 16 hours. A crystalline precipitate separated out and the slurry was poured onto excess water. The precipitate was filtered off, washed with water, dissolved in acetone and a slight precipitate filtered off. The diol was reprecipitated by the addition of water to the hot solution until cloudy then cooling to yield a white solid, m.p. 80°–90° C.

EXAMPLE XI

This example illustrates the production of 4,4'-dicarboxyphenylbenzoate using a propionic acid solvent media. The process described in Example I was carried out using a solution of 20 grams 4,4'-dimethylphenylbenzoate, 0.198 grams cobaltous bromide and 0.38 grams manganous bromide in 200 ml. propionic acid. After the composition was heated to reflux for 29 hours as oxygen was bubbled through the reaction, the flask was cooled, added to water, the precipitate filtered off, washed with water, reslurried with 5% sodium carbonate, filtered and the filtrate acidified to yield 1 gram of 4,4'-dicarboxyphenylbenzoate having an acid number of 167.

EXAMPLE XII

This example illustrates that 4,4'-dicarboxyphenylbenzoate cannot be produced by oxidation of 4,4'-dimethylphenylbenzoate with nitric acid. A slurry of 20 grams 4,4'-dimethylphenylbenzoate in 250 ml water and 50 ml fuming nitric acid were heated to reflux for four hours. The yellow crystalline material formed when the reaction was cooled, was ground in a mortar and pestle and slurry washed with 5% sodium carbonate solution for 2 hours. The precipitate was filtered off and the filtrate acidified. There was no precipitation indicating no 4,4'-dicarboxyphenylbenzoate was produced.

EXAMPLE XIII

This example illustrates the production of 4,4'-dicarboxy-2'-bromophenylbenzoate. A solution of p-toluic acid 18.2 grams, and 2-bromo-4-methylphenol 25 grams, in xylene 200 ml with sulphuric acid 0.2 ml and boric acid 0.24 grams was refluxed for 16 hours in a 500 ml flask fitted with a Dean and Stark collector. The solution was concentrated by distillation under vacuum and the residue recrystallized twice from ethanol to yield 29 grams of 4,4'-dimethyl-2'-bromophenylbenzoate m.p. 75°–80° C. Twenty-three grams of 4,4'-dimethyl-2'-bromophenylbenzoate was oxidized in 500 ml acetic acid containing 10 grams water by a catalyst composed of 2.0 grams cobalt acetate, 0.2 grams manganous acetate and 0.2 grams 48% hydrobromic acid at a temperature of 328° F. and 400 psi pressure over a 14-minute period. The oxygen uptake was 102% of theoretical. The reactor effluent, 501 grams, was filtered and the solid washed twice with glacial acetic acid and thrice with water to give 22.5 grams of a buff colored solid with an acid number of 162. (theoretical 182.)

EXAMPLE XIV

This example illustrates the production of 3,4,3',4'-tetracarboxyphenylbenzoate from 3,4,3',4'-tetramethylphenylbenzoate. 3,4,3',4'-tetramethylphenylbenzoate was prepared by refluxing 10 grams 3,4-dimethylbenzoic acid and 8.2 grams 3,4-dimethyl phenol in 100 ml xylene containing 0.1 ml sulphuric acid and 0.12 grams boric acid for 16 hours in a 250 ml flask fitted with a Dean and Stark collector. The solution was cooled to −20° C. and the crystallized material filtered off and recrystallized from ethanol to yield 11.5 grams of 3,4,3',4'-tetramethylphenylbenzoate, m.p. 100°–105° C. This material was oxidized under identical catalyst and oxidation conditions as in Example XIII. The run required 11 minutes for completion. The reactor effluent, 498 grams, was a clear solution with a slight haze due to catalyst residues. The solution was concentrated under vacuum to yield a red oil which was extracted with ethanol leaving a purple residue 2.9 grams, The alcoholic filtrate was concentrated and gave 9 grams of material after drying in a vacuum oven. The molecular weight/carboxyl was 130. The theoretical for the fully oxidized tetra acid is 99.5.

EXAMPLE XV

This example illustrates the production of 3'-4,4'-tricarboxyphenylbenzoate from 3'-4,4'-trimethylphenylbenzoate. 3,4-dimethylphenyl 24.4 grams, and p-toluic acid 27.2 grams, were refluxed together in a 1-liter flask fitted with a Dean and Stark receiver in xylene 500 ml containing sulphuric acid 0.25 ml and boric acid 0.3 grams for 24 hours. The solution was concentrated to 100 ml and cooled to give a precipitate that was filtered off and recrystallized twice from xylene. Yield 29.2 grams of 3',4,4'-trimethylphenylbenzoate, m.p. 105°–108° C. This material, 25.6 grams, was oxidized under the same conditions as employed in Example XIII. The experiment required 14 minutes for complete oxidation. The reactor effluent, 503 grams was filtered and the solid washed twice with glacial acetic acid and thrice with water to give 25 grams of an off-white solid molecular weight/carboxyl was 109. Theoretical 110.

3,5,4'-tricarboxyphenylbenzoate; 2,2',4,4'-tetracarboxyphenylbenzoate; 4,4'-dicarboxy-3-nitrophenylbenzoate; 4,4'-dicarboxy-3-chloro phenylbenzoate; 4,4'-dicarboxy-2-chloro phenylbenzoate and 4,6'-dicarboxy-2-naphthylbenzoate can be prepared by the technique of Example XIII using as a starting material respectively 3,5,4'-trimethylphenylbenzoate; 2,2',4,4'-tetramethylphenylbenzoate; 4,4'-dimethyl-3-nitrophenylbenzoate; 4,4'-dimethyl-3-chloro phenylbenzoate; 4,4'-dimethyl-2-chloro phenylbenzoate; and 4,6'-dimethyl-2-naphthylbenzoate.

We claim:
1. 3,4,3',4'-tetracarboxyphenylbenzoate.
2. 3',4,4'-tricarboxyphenylbenzoate.

* * * * *